(12) United States Patent
Kokish

(10) Patent No.: US 7,152,452 B2
(45) Date of Patent: Dec. 26, 2006

(54) ASSEMBLY FOR CRIMPING AN INTRALUMINAL DEVICE AND METHOD OF USE

(75) Inventor: Arkady Kokish, Los Gatos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 766 days.

(21) Appl. No.: 10/330,016

(22) Filed: Dec. 26, 2002

(65) Prior Publication Data
US 2004/0123437 A1 Jul. 1, 2004

(51) Int. Cl.
*B21D 41/04* (2006.01)
(52) U.S. Cl. .................. 72/402; 29/282; 29/283.5
(58) Field of Classification Search .............. 72/402, 72/416; 29/237, 283.5, 282
See application file for complete search history.

(56) References Cited

U.S. PATENT DOCUMENTS

| | | | |
|---|---|---|---|
| 3,135,310 A * | 6/1964 | Stoltz ........................... 72/397 |
| 4,034,592 A * | 7/1977 | Chen et al. .................... 72/402 |
| 4,578,982 A | 4/1986 | Schrock |
| 4,614,107 A | 9/1986 | Norin |
| 4,854,031 A | 8/1989 | Eisenzimmer |
| 5,261,263 A | 11/1993 | Whitesell |
| 5,381,686 A | 1/1995 | Thorup |
| 5,411,521 A | 5/1995 | Putnam et al. |
| 5,437,083 A | 8/1995 | Williams et al. |
| 5,509,184 A | 4/1996 | Herrero |
| 5,546,646 A | 8/1996 | Williams et al. |
| 5,626,604 A | 5/1997 | Cottone, Jr. |
| 5,630,830 A | 5/1997 | Verbeek |
| 5,658,181 A | 8/1997 | Brown, II |
| 5,672,169 A | 9/1997 | Verbeek |
| 5,715,723 A | 2/1998 | Owens |
| 5,725,519 A | 3/1998 | Penner et al. |
| 5,738,674 A | 4/1998 | Williams et al. |
| 5,746,764 A | 5/1998 | Green et al. |
| 5,810,838 A | 9/1998 | Solar |
| 5,836,952 A | 11/1998 | Davis et al. |
| 5,860,966 A | 1/1999 | Tower |
| 6,176,116 B1 * | 1/2001 | Wilhelm et al. .......... 72/409.12 |
| 6,387,117 B1 * | 5/2002 | Arnold et al. ............... 623/1.1 |
| 6,519,998 B1 * | 2/2003 | Ertl et al. ..................... 72/402 |

* cited by examiner

*Primary Examiner*—Daniel C. Crane
(74) *Attorney, Agent, or Firm*—Fulwider Patton LLP

(57) ABSTRACT

An assembly is provided which can crimp or compress an intraluminal device or measure the radial strength of an intraluminal device. The crimping assembly includes at least two moving-element subassemblies, each with a pair of moving elements. The moving elements having a first side and a second side joining at a tip. The moving-element subassembly is able to move in such a way that the moving elements move relative to each other from a first position with the tips offset from each other by a first distance, to a second position with the tips offset from each other by a second distance different than the first distance. The assembly also includes a movement assembly that interfaces with each of the moving-element subassemblies. The movement assembly moves the pairs of moving elements between the first position and the second position.

33 Claims, 9 Drawing Sheets

ASSEMBLY FOR CRIMPING AN INTRALUMINAL DEVICE AND METHOD OF USE

BACKGROUND OF THE INVENTION

The present invention relates to an apparatus for loading an intraluminal device, such as a stent or an embolic device such as a filter, onto the distal end of a catheter assembly similar to those used, for example, in percutaneous transluminal coronary angioplasty (PTCA) procedures or in percutaneous transluminal angioplasty (PTA) procedures. The present invention device is useful in crimping balloon-expandable stents and self-expanding stents.

In typical PTCA procedures, a guiding catheter is percutaneously introduced into the cardiovascular system of a patient through the brachial or femoral arteries and advanced through the vasculature until the distal end of the guiding catheter is in the ostium of the aorta leading to the coronary arteries. A guide wire and a dilatation catheter having a balloon on the distal end are introduced through the guiding catheter with the guide wire sliding within the dilatation catheter. The guide wire is first advanced out of the guiding catheter into the patient's coronary vasculature and the dilatation catheter is advanced over the previously advanced guide wire until the dilatation balloon is properly positioned across the arterial lesion. Once in position across the lesion, a flexible and expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, restenosis of the artery may develop at or near the treatment area, which may require another angioplasty procedure, a surgical bypass operation, or some other method of repairing or strengthening the area. To reduce the likelihood of the development of restenosis and to strengthen the area, a physician can implant an intravascular prosthesis for maintaining vascular patency, commonly known as a stent, inside the artery at the treated area. The stent is transported in its low profile delivery diameter through the patient's vasculature. At the deployment site, the stent is expanded to a larger diameter, often by inflating the balloon portion of the catheter. The stent also may be of the self-expanding type.

Since the catheter and stent travel through the patient's vasculature, and typically through the coronary arteries, the stent must have a small delivery diameter and must be firmly attached to the catheter until the physician is ready to implant it. Thus, the stent must be loaded onto the catheter so that it does not interfere with delivery, and it must not come off the catheter until it is implanted.

In procedures where the stent is placed over the balloon portion of the catheter, it is necessary to crimp the stent onto the balloon portion to reduce its diameter and to prevent it from sliding off the catheter when the catheter is advanced through the patient's vasculature. Non-uniform crimping can result in sharp edges being formed along the now uneven surface of the crimped stent. Furthermore, non-uniform stent crimping may not achieve the desired minimal profile for the stent and catheter assembly. Where the stent is not reliably crimped onto the catheter, the stent may slide off the catheter and into the patient's vasculature prematurely as a loose foreign body, possibly causing blood clots in the vasculature, including thrombosis. Therefore, it is important to ensure the proper crimping of a stent onto a catheter in a uniform and reliable manner.

This crimping is sometimes done by hand, which can be unsatisfactory due to the uneven application of force resulting in non-uniform crimps. In addition, it is difficult to visually judge when a uniform and reliable crimp has been applied.

Some self-expanding stents are difficult to load by hand into a delivery device such as a catheter. Self-expanding stents typically are compressed or crimped to a small diameter and then inserted into a delivery catheter where the stent remains until it is pushed out and expands into the vessel. Further, the more the stent is handled the higher the likelihood of human error, which would be antithetical to a properly crimped stent. Accordingly, there is a need in the art for a device for reliably crimping or compressing a self-expanding stent and inserting it into a catheter.

There have been attempts at devising a tool for crimping a stent onto a balloon delivery catheter. An example of such a tool comprises a series of plates having substantially flat and parallel surfaces that move in a rectilinear fashion with respect to each other. A stent carrying catheter is disposed between these surfaces, which surfaces crimp the stent onto the outside of the catheter by their relative motion and applied pressure. The plates have multiple degrees of freedom and may have force-indicating transducers to measure and indicate the force applied to the catheter during crimping of the stent.

Another stent loading tool design is comprised of a tubular member housing a bladder. The tubular member and bladder are constructed to hold a stent that is to be crimped onto a balloon catheter assembly. Upon placement of the stent over the balloon portion of the catheter, a valve in the loading tool is activated to inflate the bladder. The bladder compresses the stent radially inward to a reduced diameter onto the balloon portion of the catheter to achieve a snug fit. In this way, the stent is crimped onto the distal end of a balloon catheter with a minimum of human handling. The foregoing stent crimping tools are disclosed in, for example, commonly owned and assigned U.S. Pat. Nos. 5,437,083 and 5,546,646 to Williams et al.

Yet another stent crimping tool is known in the art as the BARD XT, which is actually a stent loader. It is constructed of a tubular body with a ball at one end connected to a plurality of long, thin strips passing through the rigid tubular body. An uncrimped stent is placed over the plurality of long, thin strips, which hold the stent in an expanded state. The balloon portion of a catheter is inserted into the cylindrical space formed by the plurality of strips. When the user pulls on the ball while holding the tubular body against the stent, the strips are slid from beneath the stent and the stent is transferred onto the balloon portion.

Still another conventional stent crimping tool is manufactured by JOHNSON & JOHNSON and appears similar to a hinged nutcracker. Specifically, the tool is comprised of two hand operated levers hinged at one end and gripped in the palm of the hand at the opposite end. A cylindrical opening holding a crimping tube is provided through the mid-portion of the tool to receive therein a stent loaded onto a balloon catheter. The crimping operation is performed by the user squeezing the handle thereby pressing the crimping tube which in turn pinches the stent onto the balloon catheter.

While the prior art devices are suitable for crimping stents onto balloon catheters, they suffer from problems such as non-uniform crimping forces, resulting in non-uniform crimps, and they are unsuitable for use by physicians in a cath lab who desire to crimp the stent onto the balloon catheter.

SUMMARY OF THE INVENTION

The present invention provides for a stent crimping or compressing assembly that is easy to use, and provides a tight and reliable crimped stent onto the distal portion of a stent delivery catheter. Preferably, the stent crimping assembly is used to crimp an expandable stent onto the balloon portion of a catheter, however, the device can be used with self-expanding stents as well. The terms crimping and compressing as used herein are meant to be interchangeable and mean that the diameter of the stent is reduced to some degree. Typically, balloon-expandable stents are known by persons having ordinary skill in the art to be "crimped" onto the balloon portion of a catheter while self-expanding stents are compressed onto a mandrel or sheath and then inserted into a catheter. Also, references to "stent crimping assembly" as used herein is not meant to be limiting since the assembly can be used as a measuring device to accurately measure the radial strength of a stent. Thus, for ease of reference, the device has been referred to throughout as a stent crimping assembly, but it also is used to measure the radial strength of a stent. Further, while reference is made herein to crimping or compressing "stents," the invention can be used with any intraluminal device to reduce the diameter or measure radial strength. Thus, the invention is particularly useful with stents, grafts, tubular prostheses, embolic devices, embolic filters, and embolic retrieval devices.

In one embodiment, the crimping assembly includes at least two moving-element subassemblies, each with a pair of moving elements. The moving elements having a first side and a second sidejoining at a tip. The moving-element subassembly is able to move in such a way that the moving elements move relative to each other from a first position with the tips offset from each other by a first distance, to a second position with the tips offset from each other by a second distance different than the first distance. The assembly also includes a movement assembly that interfaces with each of the moving-element subassemblies. The movement assembly moves the pairs of moving elements between the first position and the second position.

In one method of crimping an intraluminal device, a catheter, a mandrel or a sheath having a premounted intraluminal device is positioned within an opening formed by a plurality of moving-element subassemblies. Each moving-element subassembly has a pair of moving elements, each with a tip. The moving elements are moved relative to each other from a first position with the tips offset from each other by a first distance, to a second position with the tips moving toward the center of the opening and being offset from each other by a second distance less than the first distance. The intraluminal device is compressed onto the catheter, mandrel or sheath by continuing to move the tips of the moving elements toward the center of the opening.

In another embodiment of the invention, the device is used to measure the radial force of a stent. In this configuration, instead of crimping a stent, an expanded or unexpanded stent is placed in the device with the moving elements in the open position. The moving elements are moved toward the closed position as previously described and into contact with the stent. The radial force of the stent is measured by continuing to move the moving elements toward the closed position. The radial force of the stent is measured by using strain gauges, the geometric position of the moving elements, or similar means, to measure the radial resistance of the stent as the wedges continue to move toward the closed position.

These and other advantages of the present invention will become more apparent from the following description thereof when taken in conjunction with the following drawings.

DETAILED DESCRIPTION OF THE PREFERRED EMBODIMENTS

The present invention stent crimping assembly provides for a reliable and uniform crimp of any stent onto a catheter. The stent crimping assembly is capable of crimping almost any size stent, or length of stent, onto the distal portion of a catheter, including stents for coronary arteries and peripheral arteries. The terms crimping and compressing as used herein are meant to be interchangeable and mean that the diameter of the stent is reduced to some degree. Typically, balloon-expandable stents are known by persons having ordinary skill in the art to be "crimped" onto the balloon portion of a catheter while self-expanding stents are compressed onto a mandrel or sheath and then inserted into a catheter. Also, references to "stent crimping assembly" as used herein is not meant to be limiting since the assembly can be used as a measuring device to accurately measure the radial strength of a stent. Thus, for ease of reference, the device has been referred to throughout as a stent crimping assembly, but it also is used to measure the radial strength of a stent. Further, while reference is made herein to crimping or compressing "stents," the invention can be used with any intraluminal device to reduce the diameter or measure radial strength. Thus, the invention is particularly useful with stents, grafts, tubular prostheses, embolic devices, embolic filters, and embolic retrieval devices.

The present invention also can be used to compress a self-expanding stent onto a mandrel or a sheath and then insert the compressed stent into a catheter for subsequent use to repair a vessel. The present invention also can be used to measure the radial force of an expanded or unexpanded stent.

Figure 1:
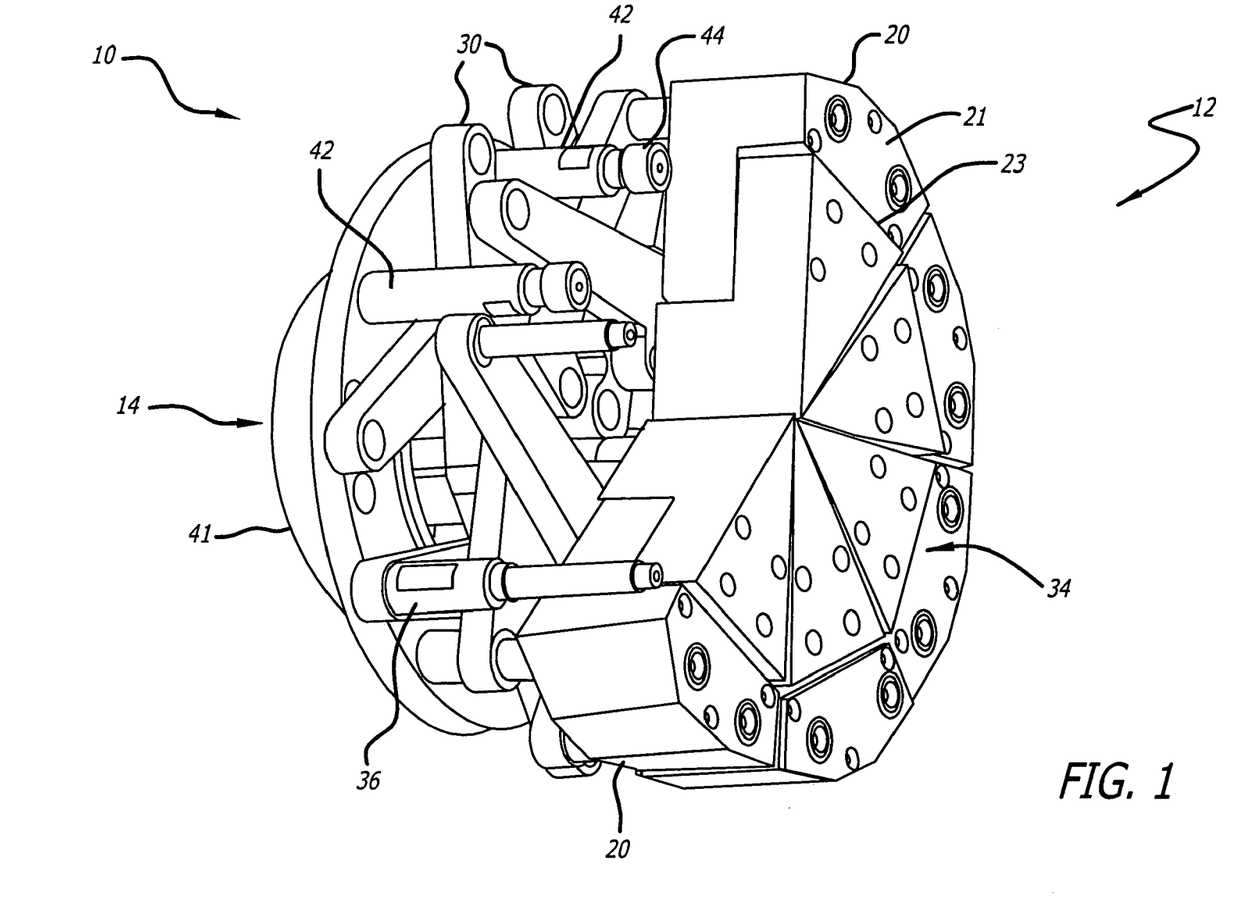
FIG. 1 depicts a first perspective view of a stent crimping assembly including a moving-element assembly, a drive-wheel assembly and a base assembly, with the base assembly and portions of the moving element assembly and drive-wheel assembly removed for clarity.
Figure 2:
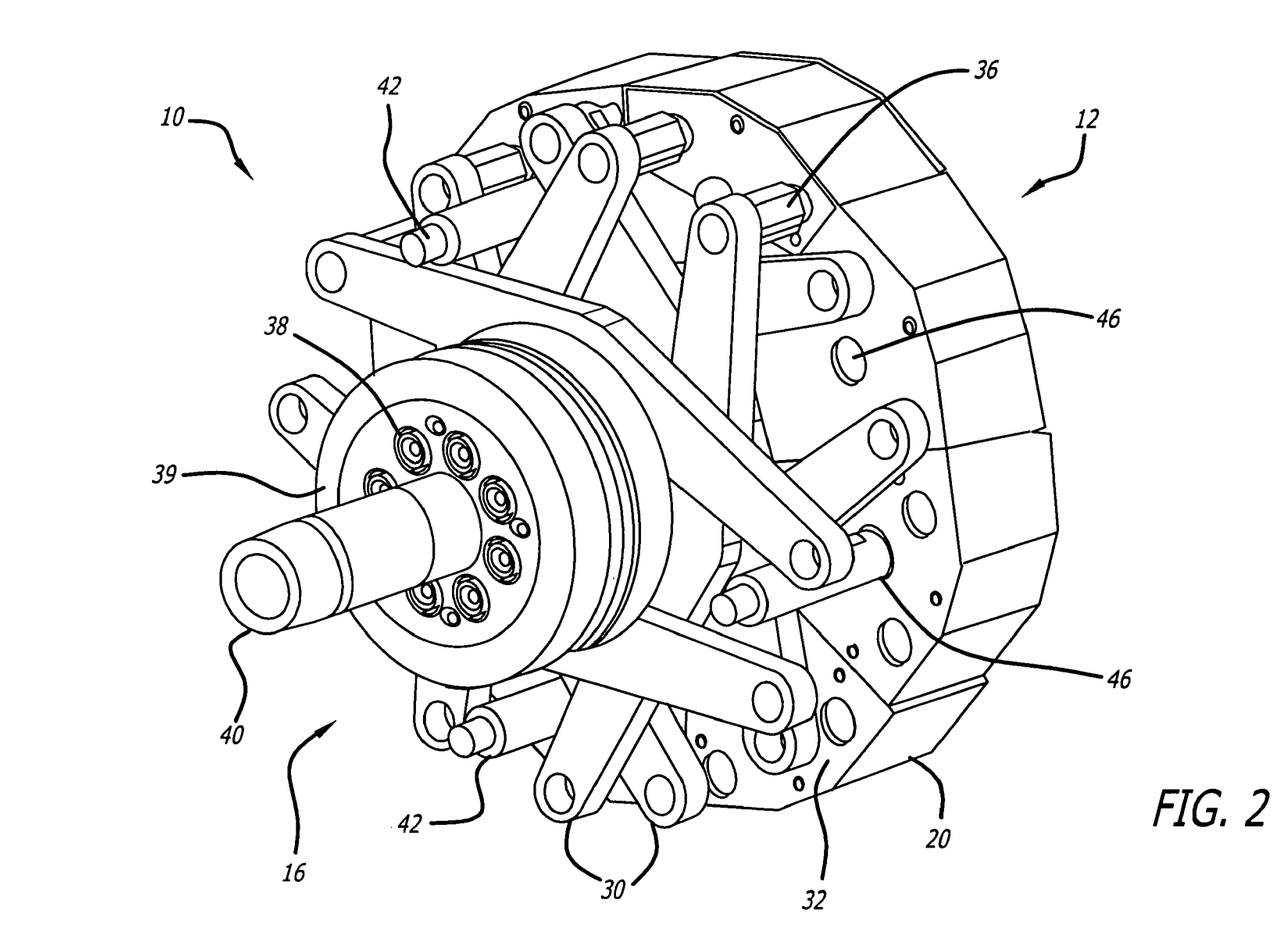
FIG. 2 depicts a second perspective view of the stent crimping assembly of FIG. 1 including the moving-element assembly and the base assembly, with portions of each assembly removed for clarity.
Figure 3:
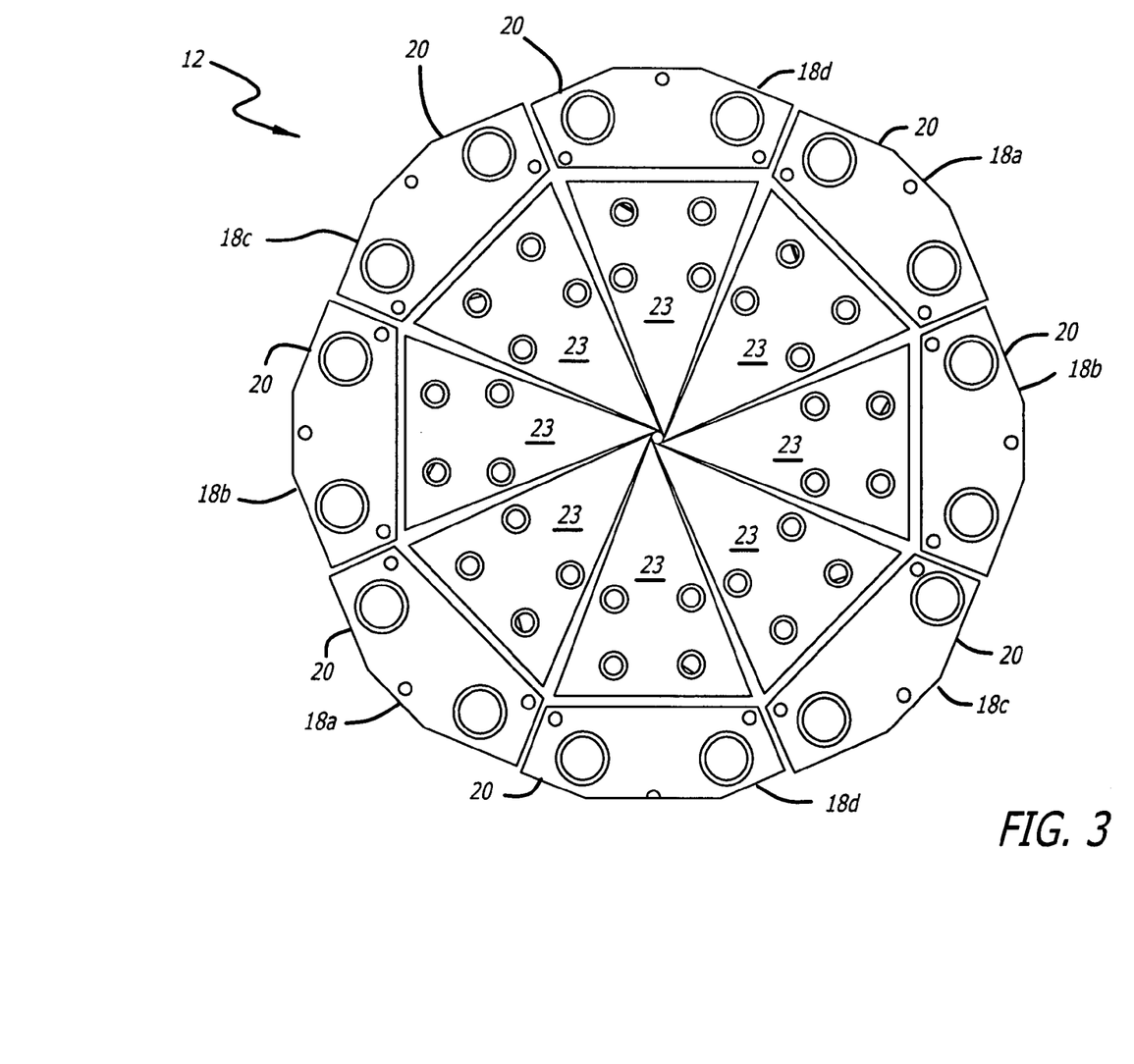
FIG. 3 depicts a front view of the moving-element assembly of FIGS. 1 and 2 and including four moving-element subassemblies.

With reference to FIGS. 1, 2 and 3, the stent crimping assembly 10 includes a moving-element assembly 12, a drive-wheel assembly 14 and a base assembly 16. In the configuration shown, the moving-element assembly 12 includes four moving-element subassemblies 18a, 18b, 18c, 18d, with a portion of each subassembly interposed between portions of adjacent subassemblies.

Figure 4:
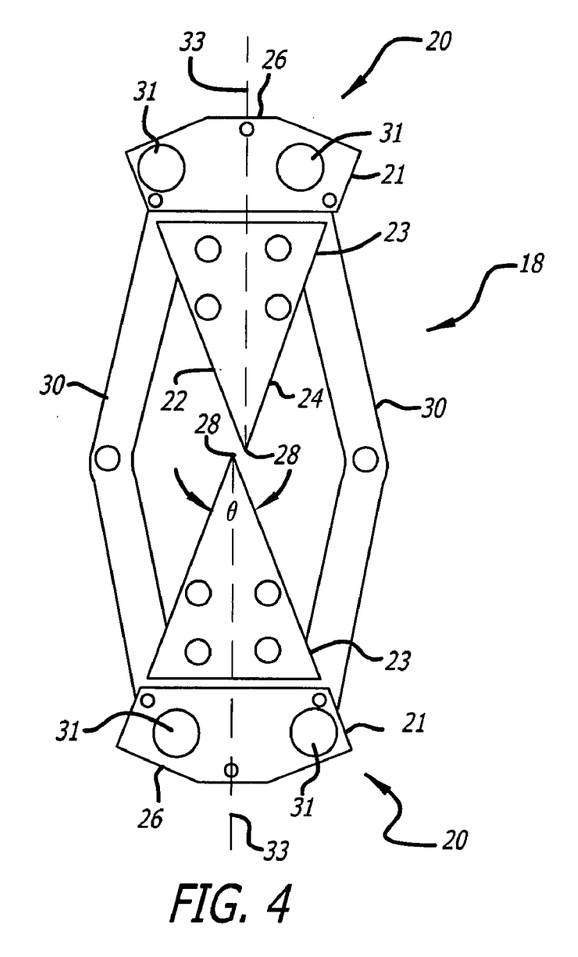
FIG. 4 depicts a front view of a moving-element subassembly.

With reference to FIGS. 1 and 4, each of the moving-element subassemblies 18 includes a pair of moving elements 20, each of which includes a bracket 21 and a wedge 23. Each of the wedges 23 attaches to its respective bracket 21 by any convenient means, including attachment screws, adhesives, and the like. In an alternate configuration, the bracket 21 and wedge 23 are formed as one piece.

With continued reference to FIG. 4, each moving element 20 includes a first side 22 and a second side 24 defined by the wedge 23 and a back side 26 defined by the bracket 21. The first side 22 and the second side 24 join together at a tip 28 and define a moving-element angle θ. The moving elements 20 are coupled together by a pair of pivot links 30, or linking means, such that the moving elements are arranged in a mirror like, opposing relationship with their tips 28 and back sides 26 facing each other.

The pivot links 30 interface with the brackets 21 at attachment points 31. As evident in FIG. 4, the attachment points 31 are asymmetrically positioned relative to the center line 33 of the moving element 20. Such positioning causes the moving-element subassembly 18 to form a tilted parallelogram when the moving elements 20 are aligned along their center lines 33. This tilted parallelogram effect is described further below with respect to FIGS. 6a, 6b and 6c.

With continued reference to FIG. 4, the first side 22 of the moving element includes a section that comes into contact with a stent and crimps it onto a catheter. This section of the moving element is substantially linear, is in the region near the tip 28 and is referred to as the stent— or device-contacting section, region or portion.

With reference to FIGS. 1 and 2, each of the moving elements 20 has a back face 32 (FIG. 2) which faces the pivot links 30 and a front face 34 (FIG. 1) opposite the back face 32. As previously mentioned, each of the brackets 21 of the moving elements 20 within a moving-element subassembly 18 interfaces with the pivot links 30. This interface is provided by element shafts 36 that extend at one end into bores within the moving elements 20 and, at the other end into bores at the end of the pivot links 30. In order to allow for movement of the moving-element subassemblies 18 in the manner described below, the element shafts 36 are rotatably coupled to either one or both of the moving elements 20 and the pivot links 30.

The pivot links 30 are arranged in an overlapping fashion, accordingly, the distance between the links and the back face 32 of the moving elements 20 are different for each moving-element subassembly 18. As a result, element shafts 36 of different lengths are used in each moving-element subassembly 18.

With reference to FIG. 2, the base assembly 16 includes eight pivot shafts 38 that extend from a collar 39 toward the back faces 32 of the moving elements 20. The base assembly 16 also includes a rotating shaft 40 that is rotatably coupled to the collar 39 and extends in the direction opposite the pivot shafts 38. The collar 39 and pivot shafts 38 are stationary. Each of the pivot shafts 38 interfaces with one of the pivot links 30 through a whole at the center of the link. As described further below, during movement of the moving-element subassemblies 18, each of the pivot links 30 pivots about its respective pivot shaft 38. The pivot shafts 38 are spaced a distance from the moving elements 20. Thus the points about which the moving elements 20 pivot are off of the moving element, i.e., they do not directly interface with the moving elements.

With reference to FIG. 1, the drive-wheel assembly 14 is rotatably coupled to the shaft 40 (not shown) and includes a drive wheel 41 and eight drive shafts 42 which extend toward the back side of the moving elements 20. The drive-wheel assembly 14 functions as a movement assembly, or moving means, that interfaces with each of the moving-element subassemblies 18 to simultaneously move the pairs of moving elements 20 between a first position and a second position. At the end of each drive shaft 42 is a roller 44. The roller 44 end of each drive shaft 42 extends into a bore 46 (FIG. 2) located in the back side of the moving element 20. As described later, rotation of the drive-wheel 14 and drive shaft 42 translates to movement of the moving elements 20. The roller 44 on the drive shaft 42 minimizes the friction between the drive shaft 42 and the moving elements 20.

Figure 10:
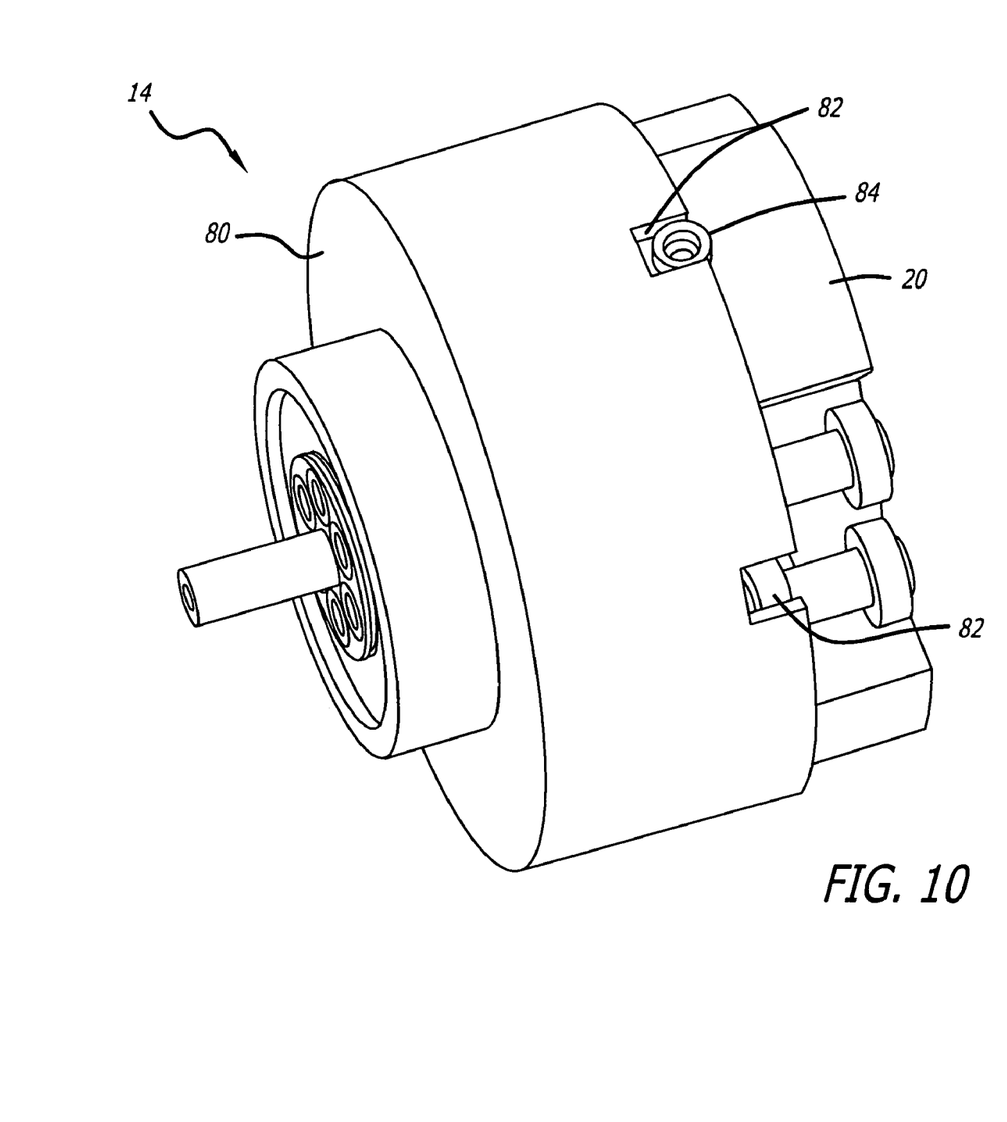
FIG. 10 depicts an alternate configuration of the drive-wheel assembly.

The movement assembly, or moving means, may include other structure functionally equivalent to the drive-wheel assembly 14 shown in FIGS. 1 and 2. For example, with reference to FIG. 10, the moving means 14 may include a drive wheel drum 80 with notches 82 that mate with members 84 protruding from the peripheral surface of the moving elements 20. In this configuration, rotation of the drums 80 translates to movement of the moving elements 20.

Rotational movement is imparted to the drive-wheel assembly 14 by rotating the rotating shaft 40 by any of a number of means. For example, a lever (not shown) may be attached to the rotating shaft 40 so that as the lever is moved in a vertical position, the shaft is rotated in either a clockwise or counterclockwise direction. Rotating the shaft 40 in turn rotates the drive-wheel assembly 14 a corresponding number of degrees. It is contemplated that other means are available to impart rotational movement to the rotating shaft 40, and in turn the drive-wheel assembly 14. For example, an electric motor (not shown) can be attached to the rotational shaft to impart rotational movement. Likewise, either hydraulic or pneumatic means may be employed to impart rotational movement to the rotating shaft 40.

The moving-element assembly 12 is moved between a first position, e.g., closed position, and a second position, e.g., opened position, by movement of the drive-wheel assembly 14. Rotation of the drive-wheel assembly 14 in a first direction, e.g., clockwise, moves the moving-element assembly 12 towards the closed position, while movement in a second direction, opposite the first direction, moves the assembly to an opened position.

Figure 5A:
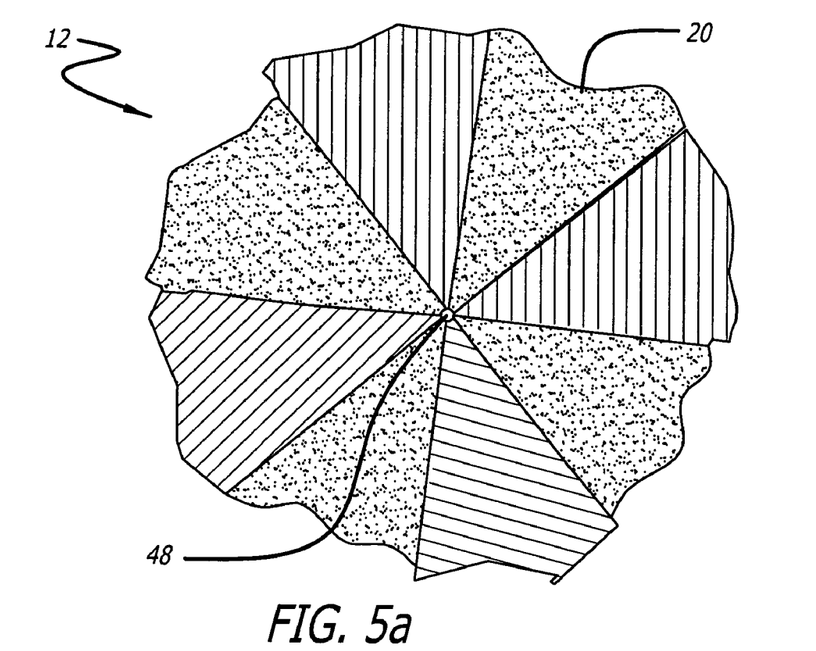
FIG. 5a is an enlarged depiction of the central portion of the moving-element assembly of FIGS. 1–3 in the closed position.
Figure 5B:
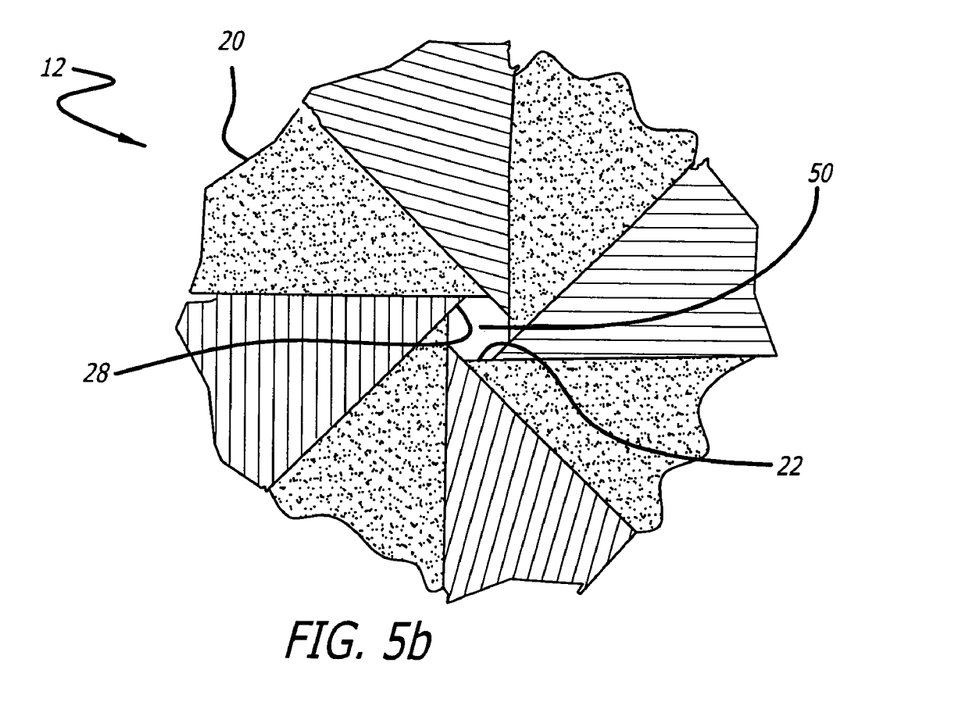
FIG. 5b is an enlarged depiction of the central portion of the moving-element assembly of FIGS. 1–3 in an opened position.

With reference to FIG. 5a, when the moving-element assembly 12 is in the closed position the tips 28 of each moving element 20 converge toward the center 48 of the assembly. With reference to FIG. 5b, when the moving-element assembly 12 is in an opened position, the moving elements 20 move to form an opening 50, with a portion of the first side 22 of each moving element defining the opening. In the configuration of FIG. 5b, eight moving elements 20 form an octagon opening 50.

With reference to FIGS. 1 and 2, in operation, rotation of the drive-wheel assembly 14 translates movement to the moving elements 20 through the drive shafts 42. Movement of the moving elements 20, in turn, translates movement to the pivot links 30 through the element shafts 36. The pivot links 30, in turn, pivot about their respective pivot shafts 38. The pivot links 30 and pivot shafts 38 function as constraining means, which control the movement of the moving elements 20, along an arcuate path, as described further below.

Figure 6A:
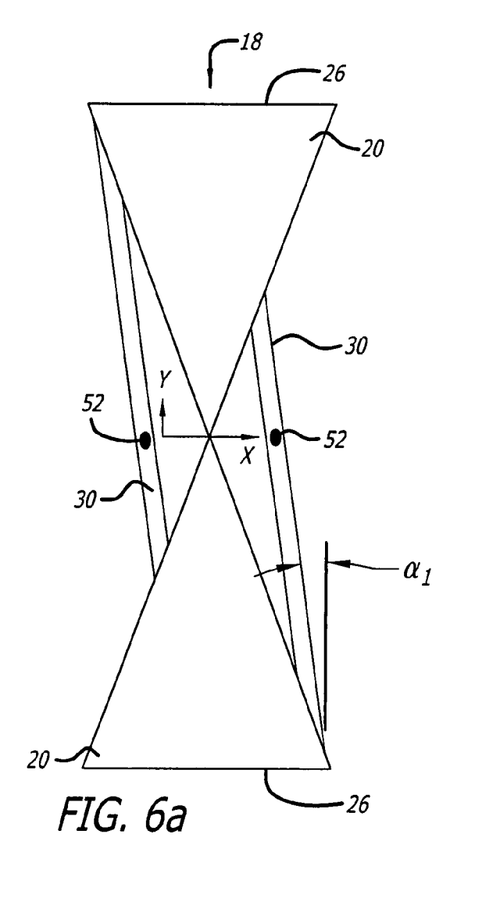
FIG. 6a is a schematic depiction of a moving-element subassembly in a closed position.
Figure 6B:
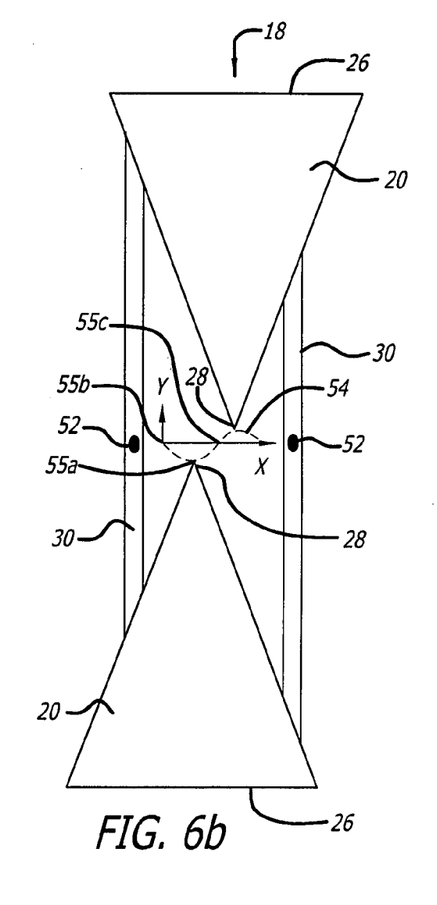
FIG. 6b is a schematic depiction of a moving-element subassembly in a first opened position.
Figure 6C:
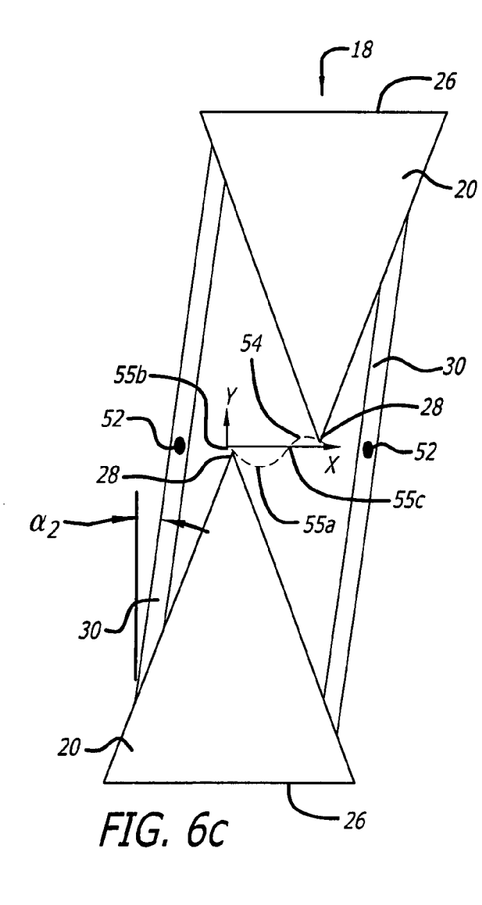
FIG. 6c is a schematic depiction of a moving-element subassembly in a second opened position.

With reference to FIGS. 6a, 6b and 6c, as previously described, each of the moving-element subassemblies 18 includes a pair of moving elements 20 coupled together by a pair of pivot links 30. The elements 20 and links 30 may be described as forming a parallelogram. When the moving-element subassembly 18 is in a closed position the parallelogram is tilted in a first direction, e.g., to the left, and has an associated tilt angle $\alpha_1$. In this closed position, the moving elements 20 are aligned in a tip-to-tip arrangement as shown in FIG. 5a.

As the assembly is moved to an open position, the moving elements 20 pivot about their respective pivot points 52 through the pivot links 30 along an arcuate path 54. When traveling along this path, the moving elements become offset from each other. When the parallelogram formed by the moving-element subassembly 18 becomes substantially rectangular, as shown in FIG. 6b, the moving elements 20 have moved away from each other in both the "x" and "y" directions, with the offset in the "y" direction being at a maximum. Each moving elements 20 moves along a curved path 54. The combination of the paths 54 form a sinusoidal like path 54 which is shown in the figures as being traced by the tips 28 of the moving elements.

As the moving-element subassembly 20 is moved to a more open position, the parallelogram tilts in a second direction, e.g., to the right, as shown in FIG. 6c, and has an associated tilt angle $\alpha_2$. As this occurs the moving elements 20 continue to move away from each other with respect to the "x" direction. With respect to the "y" direction, however, the moving elements 20 move toward each other, thus the offset in this direction decreases. When the offset in the "y" direction is substantially zero, as it is in the closed position (FIG. 6a), tilt angle $\alpha_1$ equals tilt angle $\alpha_2$.

The dual pivot-point, parallelogram arrangement of the moving-element subassemblies 18 provides for movement distinct from some conventional crimping devices which have moving elements that pivot about a single point. In these conventional devices, the moving elements trace a circular path that is generally inverse to the path traced by the assembly of the present invention. More specifically, as shown in FIGS. 6a, 6b and 6c, when moving from a closed position (FIG. 6a) to an opened position (FIG. 6c), the tips 28 of the moving elements 20 trace a path 54 that moves outward in a direction toward the back side 26 of the moving element (FIG. 6b) before moving back inward in the direction of the tip 28, thus forming an arcuate path having a tip 55a and two end points 55b, 55c, the tip of which is closer to the back side 26 of the moving element than the ends. In moving elements configured to rotate about a single pivot point located near the back side, the arcuate path traced by the tip has two ends that are closer to the back side of the moving element than the tip.

Figure 7:
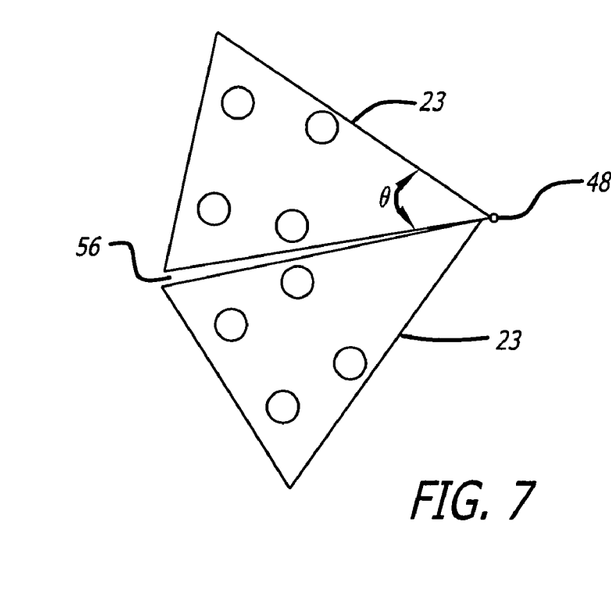
FIG. 7 depicts the spacing between adjacent moving elements.

With reference to FIG. 7, the wedges 23 of the moving elements are configured such that there is a spacing 56 between adjacent wedges. The spacing 56 increases with increased distance from the center 48 of the moving assembly and is defined by the angle θ, which is the same for each wedge 23. In order to create the spacing 56 between adjacent wedges, the summation of the θ angles for all wedges is less than 360°. In one configuration of the stent crimper, eight wedges, each having an angle θ of just less than 45°, e.g. 44.3°±0.3°, form an octagon opening.

As previously mentioned, the stent crimping assembly has an open position and a closed position as shown in FIGS. 5a and 5b. As rotational movement is imparted to the drive-wheel assembly 14, the moving elements 20 of each moving-element subassembly 18 simultaneously move away from the center of the opening formed by the moving elements and toward the open position. Movement of the moving elements 20 in the opening direction is limited by the other moving elements within the moving-element assembly. More specifically, as the moving elements 20 move toward a more opened position, they eventually reach a position where the second side 24 of each moving element abuts the first side 22 of an adjacent moving element. When this interference between adjacent moving elements occurs, further movement of the assembly is prohibited. When the drive-wheel assembly 14 is rotated in the opposite direction, the tips 28 of the moving elements move toward the center of the opening toward the closed position.

Figure 8A:
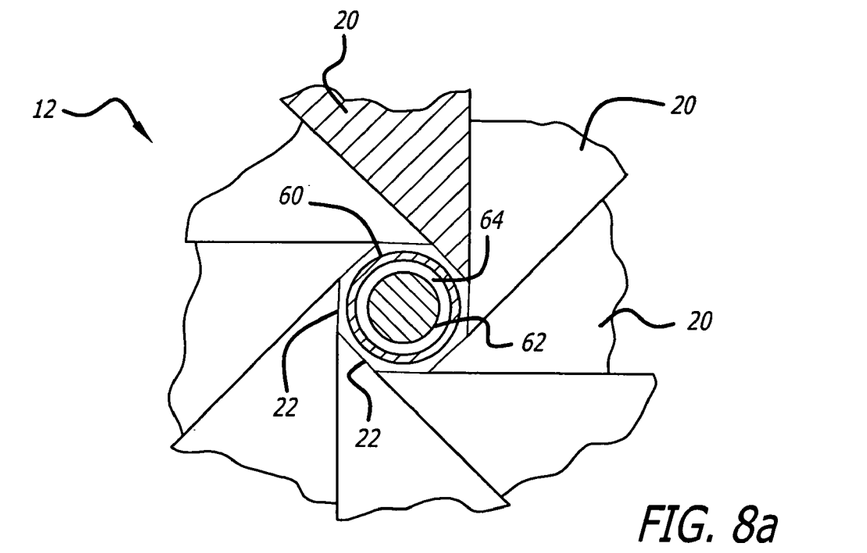
FIG. 8a depicts the moving-element assembly with a stent premounted on a catheter positioned in the opening of the assembly.
Figure 8B:
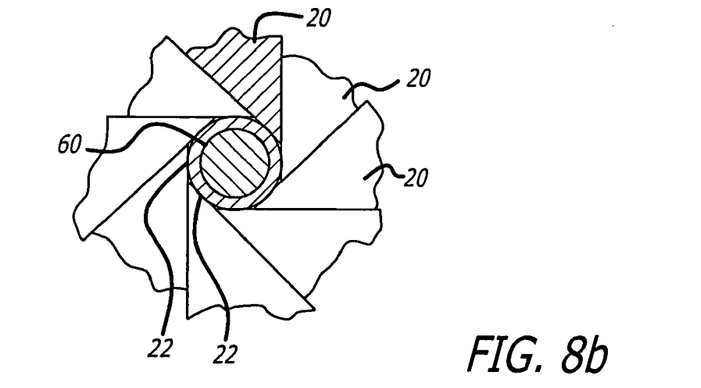
FIG. 8b depicts the moving-element assembly of FIG. 8a where the moving elements have been moved toward the closed position.
Figure 8C:
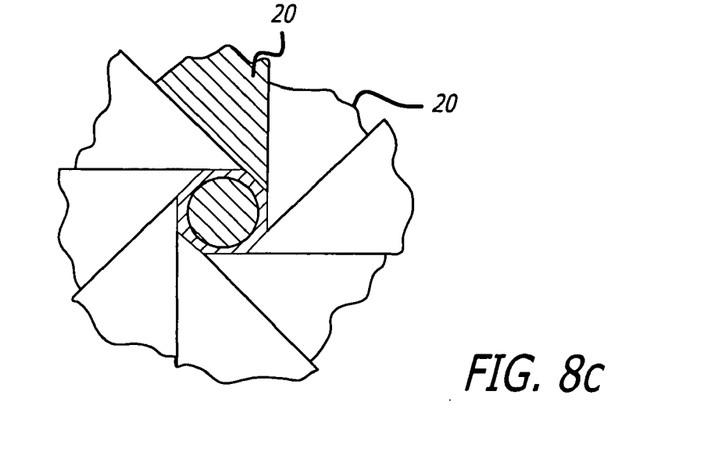
FIG. 8c depicts the moving-element assembly of FIG. 8a where the moving elements have been moved toward the closed position and into crimping engagement with the stent.

With reference to FIGS. 8a, 8b and 8c, one method for crimping a stent 60 onto a catheter 62 includes multiple applications of crimping force by the moving elements onto the stent. A stent 60 is first premounted onto a catheter 62, preferably near the distal end. The catheter 62 may have an inflatable expandable member 64, generally an inflatable balloon, upon which the stent is premounted. The stent 60 and the balloon 64 portion of the catheter are positioned within the stent crimping assembly when the moving-element assembly 12 is in the open position, as shown in FIG. 8a. The drive-wheel assembly 14 is rotated as previously described to move the moving-element assembly 12 towards the closed position.

With reference to FIG. 8b, as the moving elements 20 move toward the closed position, a portion of the device-contacting region of the first side 22 of each moving element comes into contact with the stent 60. With reference to FIG. 8c, as further rotational movement is imparted, the moving elements 20 continue to move toward the closed position thereby imparting crimping force on the stent 60. Preferably, eight moving elements 20 are used to impart crimping force on the stent 60 so that when initially crimped the stent has the appearance of an octagon when viewed under magnification. In order to form a more perfect cylinder on the stent 60, it may be desirable to repeatedly crimp the stent by slightly rotating the stent and catheter 62 a few degrees and then applying further crimping force. The opening and closing of the moving elements 20 in this manner provides a substantially cylindrical tent 60 that is tightly crimped onto the catheter 62.

It may be desirable to measure or limit the amount of force imparted by the moving elements 20 onto the stent. This can be accomplished by any number of means including providing mechanical or electrical stopping switches which limit the closing position of the moving elements. By limiting how far the moving elements can close, the amount of force also is limited. The geometric position of the moving elements also can indicate how much force is being applied to the stent. Strain gauges also can be attached to the moving elements to measure the amount of force being applied to the stent and catheter and can be controlled and monitored to limit the amount of crimping force applied to the stent.

In an alternative embodiment, the stent crimping assembly 10 can be indexed a preselected number of degrees N 71. In this embodiment, the stent and catheter are held stationary within the opening of the stent crimping assembly. The stent is crimped in the manner described, and then the stent crimping assembly is rotated N number of degrees form a 0° position and crimping force is again applied. This procedure is repeated each time the stent crimping assembly is indexed N number of degrees. As an example, the stent crimping assembly can be indexed starting from a 0° position every 5° up to 45°, and at every 5° position, the stent is crimped. The stent crimping assembly is then moved back to the 0° position and rotated in the opposite direction in 5° increments for 45°, and the stent is crimped at each 5° increment. By crimping the stent multiple times at various degrees along the cylinder, the stent is more uniformly and tightly crimped onto the balloon portion of the catheter so that under magnification it will appear as a substantially perfect cylinder.

The stent crimping assembly may be formed of plastic and metal parts, however, either all plastic or all metal, or a combination of both, is desirable. For example, both the drive-wheel assembly 14 and base assembly 16 can be formed of a polymer including a hard plastic that is machinable. The wedges 23 and brackets 21 also can be formed of a polymer that is machinable so that precise tolerances can be machined into the wedge angle θ to insure that the moving elements 20 can move toward the closed position without interfering with each other. The rotating shaft 40 can be formed of a conventional shaft material and all attachments can be in the form of metal screws, adhesives or any other conventional attachment means.

In a preferred embodiment, most of the parts of the stent crimping assembly 10 are made from machined polymers, however, the present invention is also well suited to be made from surgical steel, aluminum, or other metals so that it can be used multiple times.

Figure 9:
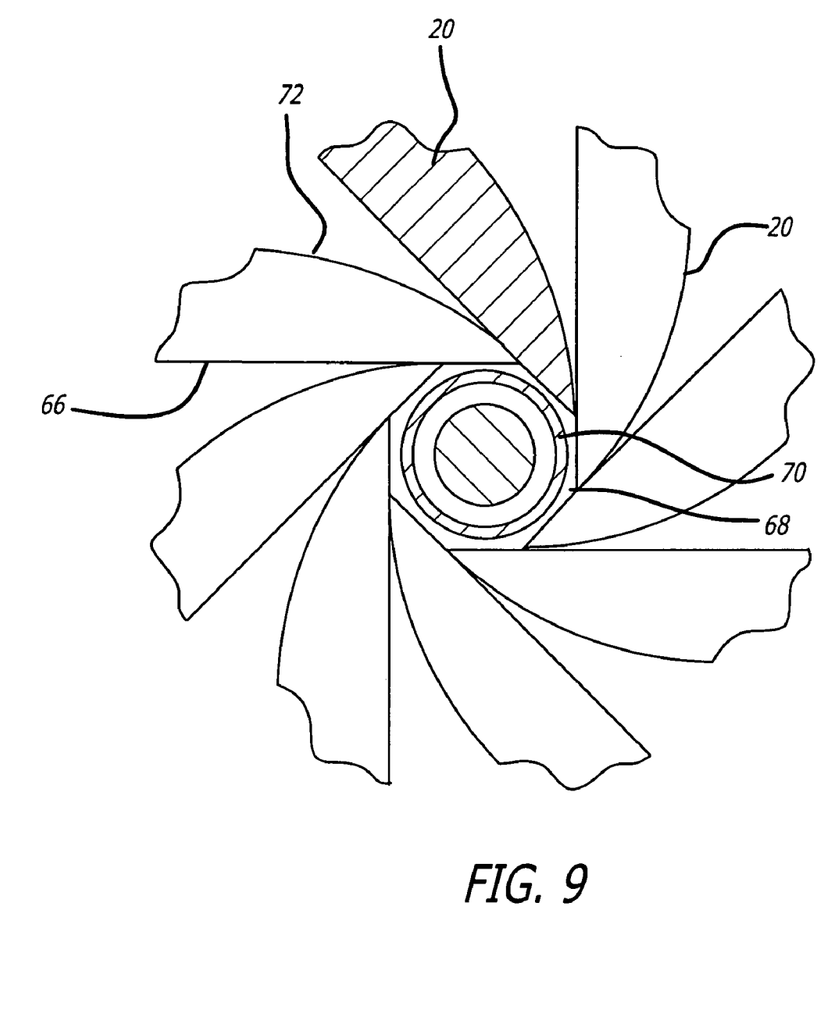
FIG. 9 depicts an alternate configuration of the moving-element assembly.

With reference to FIG. 9, as previously mention, the moving elements 20 may have anyone of a variety of shapes, as long as one side of the element includes a substantially straight region for contacting the stent, i.e., the stent-contacting region. To this end, in an exemplary alternate configuration, the moving elements 20 are shaped like knife blades, with a straight side 66 facing the opening 68 where a stent 70 may be placed to thereby provide the stent-contacting region and an arcuate side 72 facing away from the opening.

Other modifications can be made to the present invention without departing from the scope thereof. For example, while the stent crimping assembly described in detail above includes four moving-element subassemblies for a total of eight moving elements, alternate configurations of the assembly may include fewer or more than this number. An assembly may be configured to have as few as two moving-element subassemblies for a total of four moving elements. The number of wedges used can be increased or decreased depending on the particular application. Also, the specific dimensions, procedural steps, and materials of construction are provided as examples, and substitutes are readily contemplated which do not depart from the invention.

What is claimed:

1. A crimping assembly comprising:
   at least two moving-element subassemblies, each subassembly having a pair of moving elements, each moving element having a first side and a second side joining at a tip, the moving-element subassembly adapted for movement wherein the moving elements move relative to each other from a first position with the tips offset from each other by a first distance, to a second position with the tips offset from each other by a second distance different than the first distance and wherein the moving-element subassemblies are arranged relative to each other such that a portion of each moving element from one moving-element subassembly is interposed between a portion of the moving elements of the other moving-element subassemblies; and
   a movement assembly interfacing with each of the moving-element subassemblies and adapted to move the pairs of moving elements between the first position and the second position.

2. The assembly of claim 1 wherein the movement assembly is adapted to move the moving-element subassemblies simultaneously.

3. The assembly of claim 1, wherein the moving-element subassemblies are arranged such that when the tips are offset by a distance an opening is formed by the moving elements.

4. The assembly of claim 3 wherein the opening formed by the moving elements is defined by a portion of the first side of each moving element.

5. The assembly of claim 3 wherein when the moving-element subassemblies are moved in a first direction, the tips of each moving element move toward the center of the opening and when the moving-element subassemblies are moved in a second direction opposite the first direction, the tips of each moving element move away from the center of the opening.

6. The assembly of claim 1, wherein the first side of each moving element includes a substantially flat region.

7. The assembly of claim 1, wherein the moving elements travel along an arcuate path when moving between the first position and the second position.

8. An assembly for crimping an intraluminal device onto a catheter, comprising:
   a plurality of moving-element subassemblies, each subassembly having a pair of opposed moving elements coupled together by a pair of pivot links each adapted to rotate about one of a plurality of pivot shafts, the moving-element subassemblies arranged relative to each other such that a portion of each moving element from one moving-element subassembly is interposed between a portion of the moving elements of the other moving-element subassemblies, each moving element having a first side and a second side joining at a tip, the moving-element subassembly adapted for movement where the moving elements move relative to each other from a first position with the tips offset from each other by a first distance to form an opening having a first size, to a second position with the tips offset from each other by a second distance to form an opening having a second size;

a drive-wheel assembly interfacing with each of the moving-element subassemblies and adapted for rotational movement to thereby move the pairs of moving elements between the first position and the second position; and a base assembly which includes the pivot shafts.

9. The assembly of claim 8 wherein the drive-wheel assembly includes a drive wheel and a plurality of drive shafts extending from the drive wheel, the drive shafts adapted to interface with the moving elements.

10. The assembly of claim 9 wherein each moving element interfaces with at least two drive shafts.

11. The assembly of claim 8 wherein rotation of the drive-wheel assembly is limited.

12. The assembly of claim 8 wherein the plurality of moving-element subassemblies comprises four moving-element subassemblies.

13. The assembly of claim 8 wherein the first side of each moving element includes a substantially linear region.

14. The assembly of claim 8 wherein the first and second sides of the moving elements are substantially linear.

15. The assembly of claim 8, wherein the moving elements travel along an arcuate path when moving between the first position and the second position.

16. The assembly of claim 8 wherein the assembly is configured such that it may be rotated relative to the intraluminal device a preselected number of degrees N.

17. The assembly of claim 16 wherein the assembly is configured such that it may be repeatedly rotated N degrees around the intraluminal device.

18. A crimping assembly comprising:
at least four moving elements arranged relative to each other to form an opening;
means for linking the moving elements to form moving-element subassemblies, each comprising a pair of moving elements, wherein the means for linking comprises a pair of links, each secured to a first moving element at a first end and a second moving element at a second end opposite the first end;
means for simultaneously moving the moving-element subassemblies; and
means for constraining the moving-element subassemblies to movement between a first position with the moving elements offset from each other a first distance and a second position with the moving elements offset from each other a second distance different from the first distance.

19. The crimping assembly of claim 18, wherein the moving-element subassemblies are arranged such that when the tips are offset by a distance an opening is formed by the moving elements.

20. The assembly of claim 18, wherein a first side of each moving element includes a substantially flat region.

21. The assembly of claim 18, wherein an opening formed by the moving elements is defined by a portion of a first side of each moving element.

22. The assembly of claim 18, wherein when the moving-element subassemblies are moved in a first direction, the tips of each moving element move toward the center of the opening and when the moving-element subassemblies are moved in a second direction opposite the first direction, the tips of each moving element move away from the center of the opening.

23. The assembly of claim 18, wherein the moving elements travel along an arcuate path when moving between the first position and the second position.

24. A crimping assembly comprising:
at least four moving elements arranged relative to each other to form an opening;
means for linking the moving elements to form moving-element subassemblies, each comprising a pair of moving elements;
means for simultaneously moving the moving-element subassemblies, wherein the means for simultaneously moving the moving element subassemblies comprises a rotatable drive-wheel and a plurality of element shafts connecting the drive-wheel to the moving elements; and
means for constraining the moving-element subassemblies to movement between a first position with the moving elements offset from each other a first distance and a second position with the moving elements offset from each other a second distance different from the first distance.

25. A crimping assembly comprising:
at least four moving elements arranged relative to each other to form an opening;
means for linking the moving elements to form moving-element subassemblies, each comprising a pair of moving elements;
means for simultaneously moving the moving-element subassemblies; and
means for constraining the moving-element subassemblies to movement between a first position with the moving elements offset from each other a first distance and a second position with the moving elements offset from each other a second distance different from the first distance, wherein the means for constraining movement of the moving-element subassemblies comprises a pair of pivot links, each secured to a first moving element at a first end and a second moving element at a second end opposite the first end and a pair of pivot shafts about which the pivot links pivot.

26. A crimping assembly comprising:
at least two moving-element subassemblies, each subassembly having a pair of moving elements, each moving element having a first side and a second side joining at a tip and a back side opposite the tip, the moving-element subassembly adapted for movement wherein the moving elements move relative to each other such that the tips of the moving elements trace a path that moves outward in a first direction toward the back side of the moving element before moving back inward in a second direction toward the tip, thus forming an arcuate path having a tip and two end points, the tip of which is closer to the back side of the moving element than the ends; and
a movement assembly interfacing with each of the moving-element subassemblies and adapted to move the pairs of moving elements in the first and second directions.

27. A crimping assembly comprising:
at least two moving-element subassemblies, each subassembly having a pair of moving elements rotatably coupled to a pair of link members, each adapted to rotate about a pivot, the moving elements and link members forming a parallelogram adapted to pivot about the pivots from a first tilted position during which the tips of the moving elements are in a closed position to a second tilted position during which the tips of the moving elements are in an opened position; and a movement assembly interfacing with each of the moving-element subassemblies and adapted to move the pairs of moving elements and link members between the first and second tilted positions.

28. The crimping assembly of claim 27, wherein the movement assembly is adapted to move the moving-element subassemblies simultaneously.

29. The crimping assembly of claim 27, wherein the moving-element subassemblies are arranged such that when the tips are offset by a distance an opening is formed by the moving elements.

30. The crimping assembly of claim 27, wherein a first side of each moving element includes a substantially flat region.

31. The crimping assembly of claim 27, wherein an opening formed by the moving elements is defined by a portion of a first side of each moving element.

32. The crimping assembly of claim 27, wherein when the moving-element subassemblies are moved in a first direction, the tips of each moving element move toward the center of the opening and when the moving-element subassemblies are moved in a second direction opposite the first direction, the tips of each moving element move away from the center of the opening.

33. The crimping assembly of claim 27, wherein the moving elements travel along an arcuate path when moving between the first position and the second position.

* * * * *

UNITED STATES PATENT AND TRADEMARK OFFICE
CERTIFICATE OF CORRECTION

PATENT NO. : 7,152,452 B2  Page 1 of 1
APPLICATION NO. : 10/330016
DATED : December 26, 2006
INVENTOR(S) : Arkady Kokish

It is certified that error appears in the above-identified patent and that said Letters Patent is hereby corrected as shown below:

Column 3,
Line 42, delete "sidejoining" and insert instead --side joining--

Column 10,
Line 37, delete "wherein-the" and insert instead --wherein the--

Signed and Sealed this

Tenth Day of April, 2007

JON W. DUDAS
*Director of the United States Patent and Trademark Office*